United States Patent [19]
Sekine

[11] Patent Number: 5,224,479
[45] Date of Patent: Jul. 6, 1993

[54] ECG DIAGNOSTIC PAD
[75] Inventor: Yukio Sekine, Saitama, Japan
[73] Assignee: Topy Enterprises Limited, Tokyo, Japan
[21] Appl. No.: 718,757
[22] Filed: Jun. 21, 1991
[51] Int. Cl.$^5$ .......................................... A61B 5/0402
[52] U.S. Cl. ..................... 128/644; 128/639; 128/696
[58] Field of Search ............... 128/639, 644, 695, 696, 128/798, 799

[56] References Cited

U.S. PATENT DOCUMENTS

| 4,608,987 | 9/1986 | Mills | 128/639 |
| 4,698,848 | 10/1987 | Buckley | 128/644 |
| 4,709,704 | 12/1987 | Lukasiewicz | 128/644 |
| 5,007,427 | 4/1991 | Suzuki et al. | 128/644 |
| 5,054,496 | 10/1991 | Wen et al. | 128/696 |

FOREIGN PATENT DOCUMENTS 147330 9/1984 European Pat. Off. .

Primary Examiner—Lee S. Cohen
Assistant Examiner—Brian L. Casler
Attorney, Agent, or Firm—Wenderoth, Lind & Ponack

[57] ABSTRACT

An ECG diagnostic pad having upper fit portions with upper limb lead electrodes, central fit portions with unipolar precordial lead electrodes and lower fit portions with flank lead electrodes is fitted onto the chest wall of a human subject. Only by attaching the pad onto the chest wall of the subject, the lead electrodes can readily be brought in close contact with the desired locations prescribed anatomically on the chest wall with accuracy.

13 Claims, 4 Drawing Sheets

ECG DIAGNOSTIC PAD

BACKGROUND OF THE INVENTION

1. Field of the Invention:

This invention relates to an electrocardiogram (ECG) diagnostic pad capable of measuring and recording electrocardiograms of the electric current detected from various parts of the body for electrocardiographic diagnostic purposes, and more particularly, to an ECG diagnostic pad having ECG electrodes which can readily be brought in contact with the anatomically prescribed parts of the body of a human subject with accuracy merely by attaching the pad onto the chest wall of the body.

2. Description of the Prior Art:

Analytical diagnostics which are made by utilization of electrocardiograms (ECG) have been generally applied for a diagnosis of cardiopathy, for example. As one of existing electrocardiographs, there has been widely used so far the so-called Holter's electrocardiograph of a portable type with a built-in cassette tape recorder for continuously detecting and recording ECG data over a long period of time.

A standard 12-lead ECG method for inducing twelve sorts of lead ECG currents from the body of a human subject by using the aforesaid portable electrocardiograph and so on has been known. In this 12-lead ECG method, bipolar limb lead ECG (Standard lead I: left arm-right arm; Standard lead II: left leg-right arm; and Standard lead III: left leg-left arm), unipolar limb lead ECG (Standard lead aVR: right arm, and left arm-left leg; Standard lead aVL: left arm, and right arm-left leg; and Standard lead aVF: left leg, and right arm-left arm), and unipolar precordial lead ECG (V1-V6) are analyzed. Namely, twelve electric potential differences which are expressed in terms of the waveforms (ECG pattern) which vary with time are detected by applying ECG lead electrodes to ten parts of the subject's body and provide information on the condition and performance of the heart.

The ECG lead electrodes for detecting bipolar and unipolar limb leads are attached onto both arms and both legs, and the ECG lead electrodes for unipolar precordial lead are attached onto the chest wall. Particularly, the unipolar precordial lead electrodes are placed at six anatomically prescribed locations on the left-hand region of the chest wall close by the heart. In most cases, a human subject or patient would enlist the aid of a doctor or other helpers to attach the ECG lead electrodes onto the surface of the subject's body and endure discomfort. Besides, the work of attaching the ECG lead electrodes requires much time and labor and proves to be troublesome.

To eliminate the aforenoted drawbacks suffered by the conventional electrocardiographs including the portable Holter's electrocardiograph, the inventor of this invention has been formerly proposed a standard 12-lead electrocardiograph in Japanese Patent Appln. Public Discl. HEI 1-265942. An ECG electrode pad is disclosed in U.S. Pat. No. 4,583,549 to MANOLI.

The aforesaid conventional ECG pads each comprises a pad base formed in a narrow strap shape having unipolar precordial lead ECG electrodes, and makes it difficult to place the ECG electrodes at the anatomically prescribed locations on the chest wall. Also, the work of attaching the ECG pad onto the proper part prescribed on the chest wall and the work of detaching the same are both relatively troublesome. For small children and aged persons, they are frequently either impossible or very difficult.

Furthermore, the works of connecting the unipolar precordial lead ECG electrodes to an external electrocardiograph or other possible instruments and connecting the bipolar and unipolar limb lead electrodes to be attached to both arms and legs of the human subject or patient to the ECG pad often become onerous and are likely to give rise to a connection mistake of the ECG electrodes.

SUMMARY OF THE INVENTION

This invention was made in consideration of the aforenoted drawbacks of the conventional standard 12-lead electrocardiograph and ECG electrode pad. Its object is to provide an ECG diagnostic pad incorporating ECG lead electrodes, which can be readily attached to the chest wall of the body of the subject so as to bring the ECG lead electrodes in contact with the desired locations anatomically prescribed on the chest wall of the body with accuracy.

Another object of this invention is to provide a portable ECG diagnostic pad of an induction type, capable of automatically recording standard 12-lead ECG data over a long time.

To attain the objects described above according to this invention there is provided an ECG diagnostic pad comprising a pad base having upper fit portions with upper limb lead electrodes, at least one central fit portion with unipolar precordial lead electrodes and lower fit portions with flank lead electrodes. An ECG control unit for detecting ECG currents from the lead electrodes in the pad base may be mounted in the pad base.

By attaching the ECG diagnostic pad to the chest wall of a human subject or patient, the upper limb lead electrodes of the upper fit portions spontaneously come into contact with the clavicle portions, the unipolar precordial lead electrodes come into contact with the anatomically prescribed locations on the midriff portion, and the flank lead electrodes of the lower fit portions come into contact with the lower flank portion, respectively.

A unit for recording ECG data detected from the subject during measurement may be incorporated into the pad base or fastening means for fixing the pad base onto the body of the human subject. As one example, the fastening means is composed of belt- or strap-like members connected to the respective upper and lower fit portions and central fit portions of the pad base.

BRIEF DESCRIPTION OF THE DRAWINGS

The other objects and features of the present invention will now be explained in detail with reference to the accompanying drawings, wherein.

DESCRIPTION OF THE PREFERRED EMBODIMENTS

Figure 1:
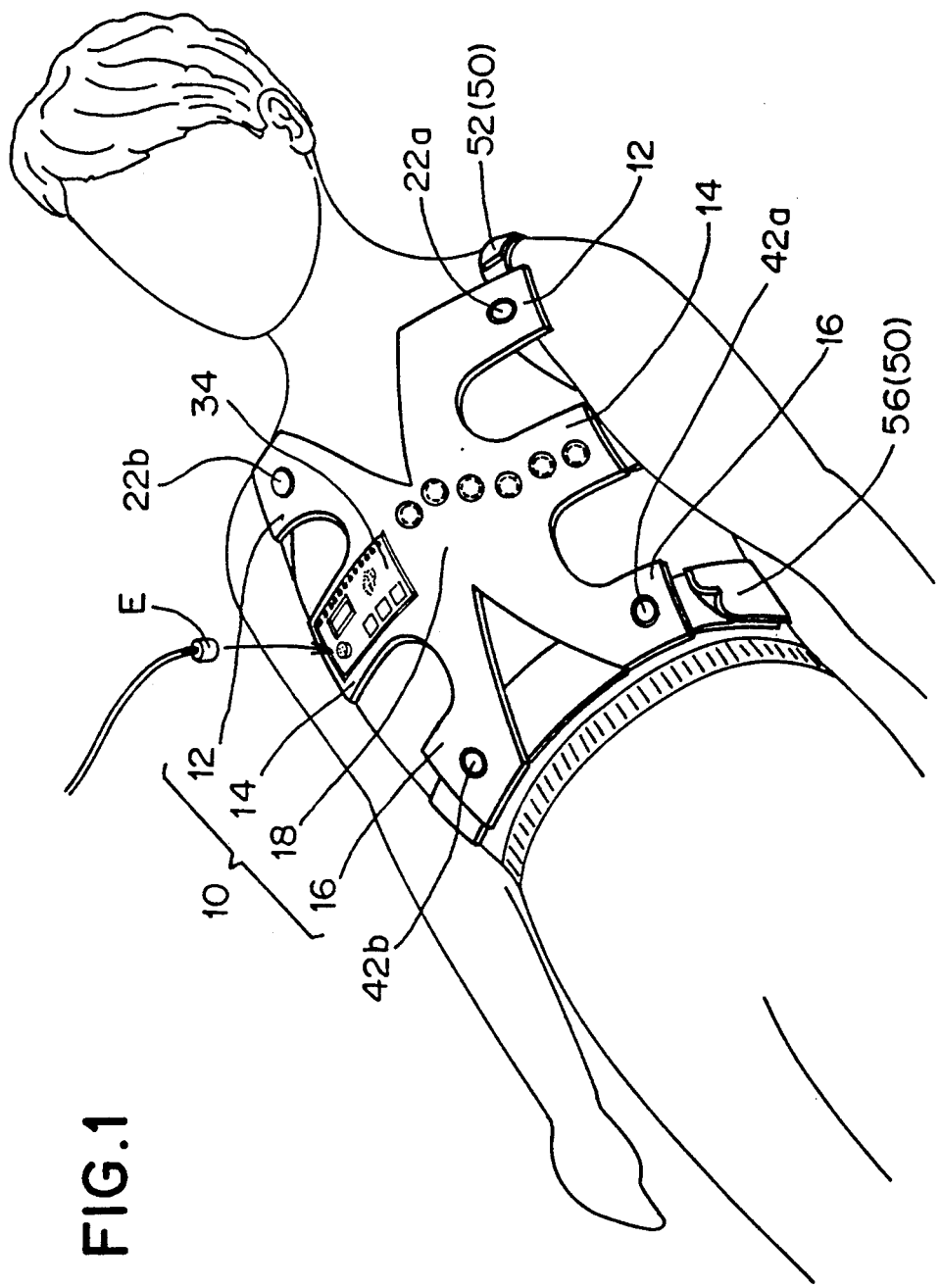
FIG. 1 is a perspective view of a human subject fitted with one embodiment of the ECG diagnostic pad according to the present invention.
Figure 2:
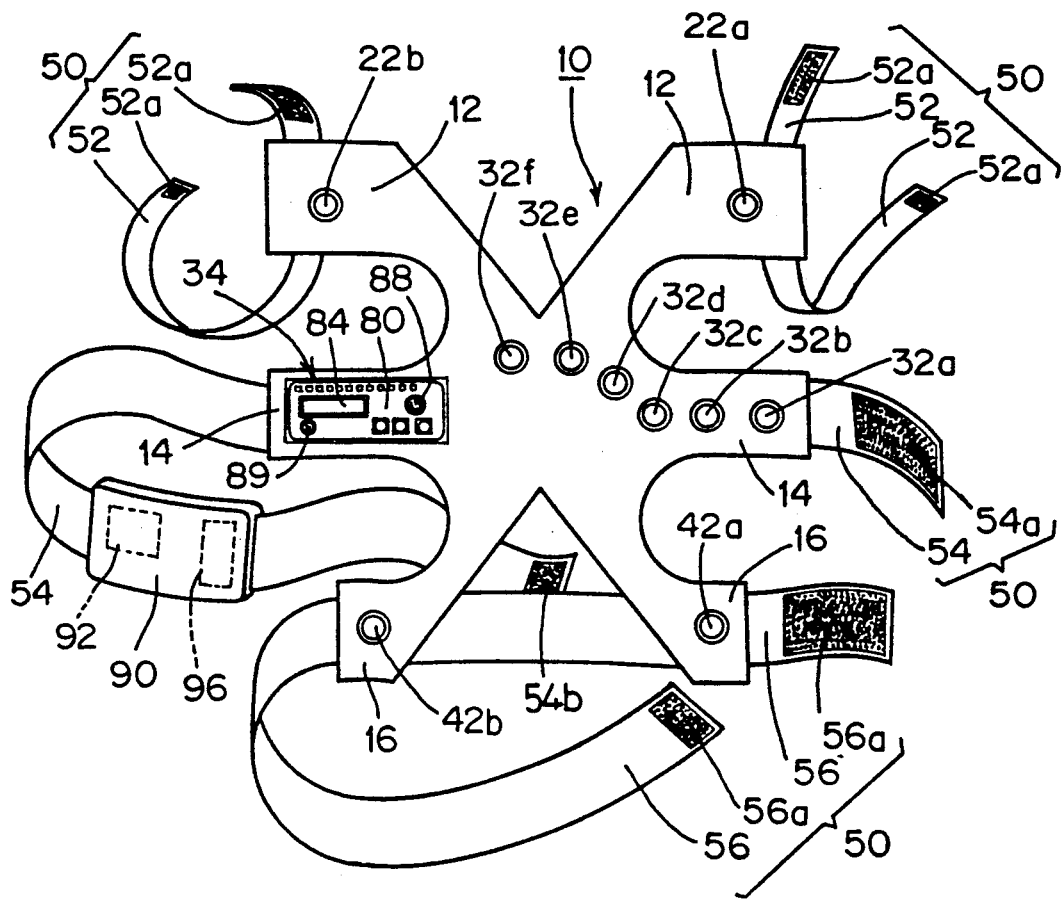
FIG. 2 is a front view of the pad of FIG. 1.

One preferred embodiment of the ECG diagnostic pad according to this invention will be described hereinafter with reference to FIGS. 1 and 2.

The ECG diagnostic pad comprises a pad base 10 made of a material having moderate flexibility together with rigidity and strength such as rubber, synthetic rubber and porous synthetic resin having, preferably, air permeability. The pad base 10 has upper fit portions 12 with upper limb lead electrodes 22a, 22b for detecting bipolar and unipolar limb lead ECG currents, central fit portions 14 with unipolar precordial lead electrodes 32a-32f, and lower fit portions 16 with flank lead electrodes 42a, 42b for detecting bipolar and unipolar limb lead ECG currents.

The pad base 10 is formed so that, when the pad base 10 is attached to the chest wall of a human subject so as to confront the center part 18 to the midriff of the subject, the upper limb lead electrodes 22a, 22b of the upper fit portions 14 spontaneously come into contact with the clavicle portions of the subject, the precordial lead electrodes 32a-32f come into contact with six locations V1-V6 prescribed on the region from the midriff to the flank of the subject, and the flank lead electrodes 42a, 42b of the lower fit portions 16 come into contact with the lower flank portion of the subject, respectively.

Since the precordial lead electrodes 32a-32f are arranged substantially on the right side of the center part 18, an ECG control unit 34 is mounted on the left side. The lead electrodes 22a, 22b, 32a-32f, 42a, 42b are electrically connected with the ECG control unit 34 by lead cables lying through the interior of the pad base.

The pad base 10 is formed in a substantially asterisk shape (combined shape of "X" and "—") to reduce the surface area thereof, namely, it has the upper fit portions 12 extending aslant upward, the central fit portions 14 extending horizontally, and the lower fit portions 16 extending aslant downward.

The pad base 10 has belt- or strap-like fastening means 50 for fixing the pad onto the body of the subject. In this embodiment, the fastening means 50 is composed of two sets of fastening belts 52 sewn onto the upper fit portions 12 to be wound around the upper arm portions of the subject, one set of fastening belts 54 sewn onto the central fit portions 14 to be wound around the breast, and one set of fastening belts 56 sewn onto the lower fit portions 16 to be wound around the trunk of the body. The belts 52, 54, 56 are provided on their free ends with surface fasteners 52a, 52b, 54a, 54b, 56a, 56b, so that they can easily be engaged with and disengaged from the respective counterparts.

Figure 3:
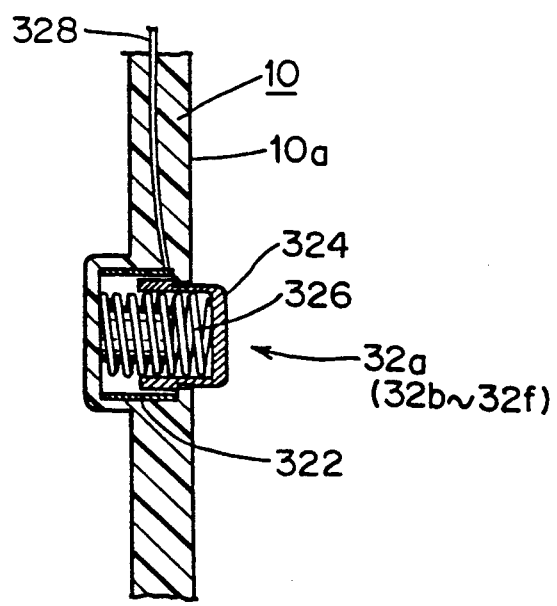
FIG. 3 is a sectioned side view of the lead electrode used in one embodiment of the present invention.

The lead electrodes 22a, 22b, 32a-32f, 42a, 42b are mounted in the pad base 10 and each comprise a holder 322, and a movable conductor 324 mounted in the holder 322 as typically illustrated in FIG. 3 representing the electrode 32a. The movable conductor 324 is urged outward from the chest-contacting side surface 10a of the pad base 10 by a spring 326. The lead electrodes 22a, 22b, 32a-32f, 42a, 42b are electrically connected to the ECG control unit 34 through lead cables 328. Therefore, by merely attaching the pad base 10 onto the chest wall of the subject, all the lead electrodes come in close contact with the chest wall with the energizing force of the spring 326 so that the desired ECG potential currents can be reliably detected.

Figure 4:
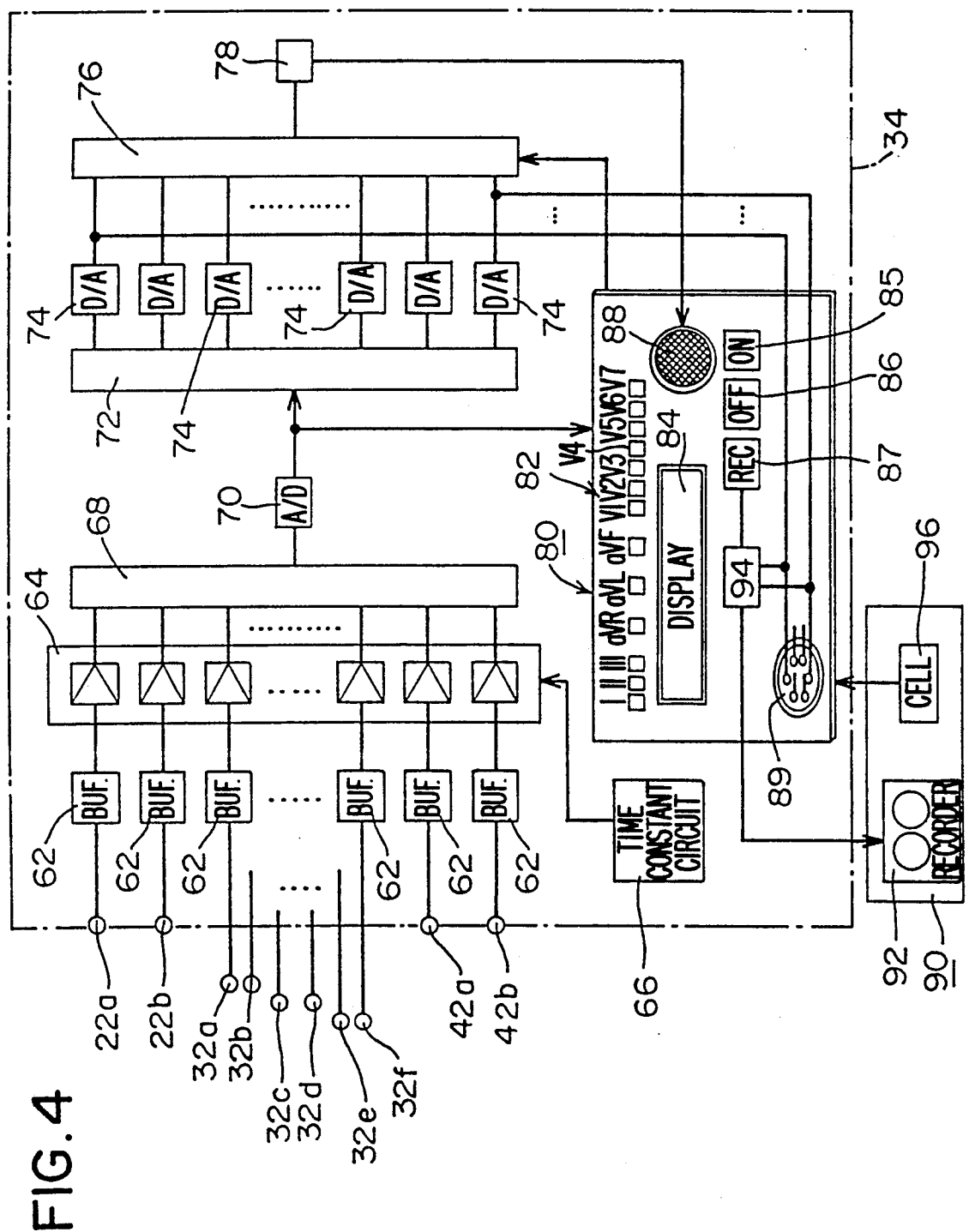
FIG. 4 is a schematic diagram showing the circuit of the ECG control unit mounted in the pad according to this invention.

The ECG control unit 34 which is mounted on the other central fit portion 14 and electrically connected to the lead electrodes 22a, 22b, 32a-32f, 42a, 42b comprises an ECG input circuit including buffers 62 for receiving ECG currents detected by the lead electrodes, an amplifier 64 for amplifying the ECG currents outputted from the ECG input circuit, a time-constant setting circuit 66 for controlling low-frequency characteristics of the ECG currents, a multiplexer 68 for outputting the ECG currents from the amplifier 64 one by one in serial order, an analog-digital converter (A/D) 70, a demodulator 72, digital-analog converters (D/A) 74, an output-stage multiplexer 76, and a sound driver 78, as illustrated in FIG. 4.

On the control panel 80 of the ECG control unit 34, there are disposed LED indicators 82 for indicating the ECG currents pulsatively derived from the subject, a display 84 such as of liquid crystal for displaying heart rate and various ECG data obtained during measurement, a power switch (ON) 85, a cutoff switch (OFF) 86, a record switch (REC) 87, a sound generator 88 connected to the sound driver 78 so as to produce the heart beat sound and so on, and an output connector 89.

On the fastening belt 54 there is mounted a recording unit 90 comprising a recording device 92 having recording medium such as an IC card and a magnetic tape recorder, and a power battery unit 96. By turning on the record switch 87 of the control unit 34, the output switch circuit 94 permits ECG data outputted from the D/A converters 74 to be fed to and recorded by the recording unit 90. The ECG control unit 34 and recording unit 90 as specified above are adopted in a common portable ECG device, and therefore, these are not indispensable constituents of this invention and by no means limitative. Though other selectors or switches are actually required for operating the time-constant setting circuit 66, multiplexer 76 and the sound driver 78, these are not illustrated in FIG. 4 due to the convenience of the explanation.

Now, the manner in which the ECG diagnostic pad according to this invention is used will be described in detail. At the outset, the pad is prepared for detecting ECG by being attached to and steadily secured onto the body of the subject by use of the fastening means 50. When attaching the pad base 10 to the chest wall of the subject while confronting the center part 18 to the midriff of the subject, all the lead electrodes 22a, 22b, 32a-32f, 42a, 42b are spontaneously placed precisely at the desired locations prescribed anatomically. That is, while the pad base 10 is attached to the chest wall of the subject, the upper limb lead electrodes 22a, 22b of the upper fit portions 14 come into contact with the clavicle portions of the subject, the precordial lead electrodes 32a-32f come into contact with six locations V1-V6 prescribed on the region from the midriff to the flank of the subject, and the flank lead electrodes 42a, 42b of the lower fit portions 16 come into contact with the lower flank portion of the subject, respectively.

Upon attachment of the pad base 10 onto the chest wall of the subject, the power switch 85 of the ECG control unit 34 is turned on to start measuring ECG potential currents for standard bipolar limb lead (I, II, III), unipolar limb lead (aVR, aVL, aVF), and unipolar precordial lead (V1-V6). Namely, ten sorts of ECG potential currents detected by the lead electrodes 22a, 22b, 32a-32f, 42a, 42b are fed to the amplifiers 64 via the buffers 62 for amplification of the ECG currents. The amplified ECG currents from the amplifiers 64 are respectively modulated to time series signals by the multiplexer 68 and further converted to digital signals by the A/D converter 70. The digital signals thus converted are distributed and synthesized by the demodulator 78 and converted to analog signals by the D/A converter 74 to give rise to twelve sorts of ECG data signals (12 lead signals). Thus, twelve lead ECG signals are derived from ten ECG potential currents detected from the subject.

By operating the recording device 92, the ECG data signals can be recorded. Through a connector plug E connected to the connector 89 on the ECG control unit 34, the ECG data signals may be outputted to an external measuring system (not shown) such as an electrocardiograph and computer.

On the other hand, the signals outputted from the D/A converter 74 is alternatively fed to the sound driver 78 through the multiplexer 76 so that the sound generator 88 is driven to produce pulse sounds responsive to the heart beat of the subject. By transmitting the pulse sounds through a telephone line or the like, it is possible to make a cardiac diagnosis on a patient at a distant place.

Though, in the illustrated embodiment, the ECG diagnostic pad is applied to the measurement of standard 12-lead EGC, the application of this pad is not specifically limited thereto and may be variously modified as the need arises.

Figure 5:
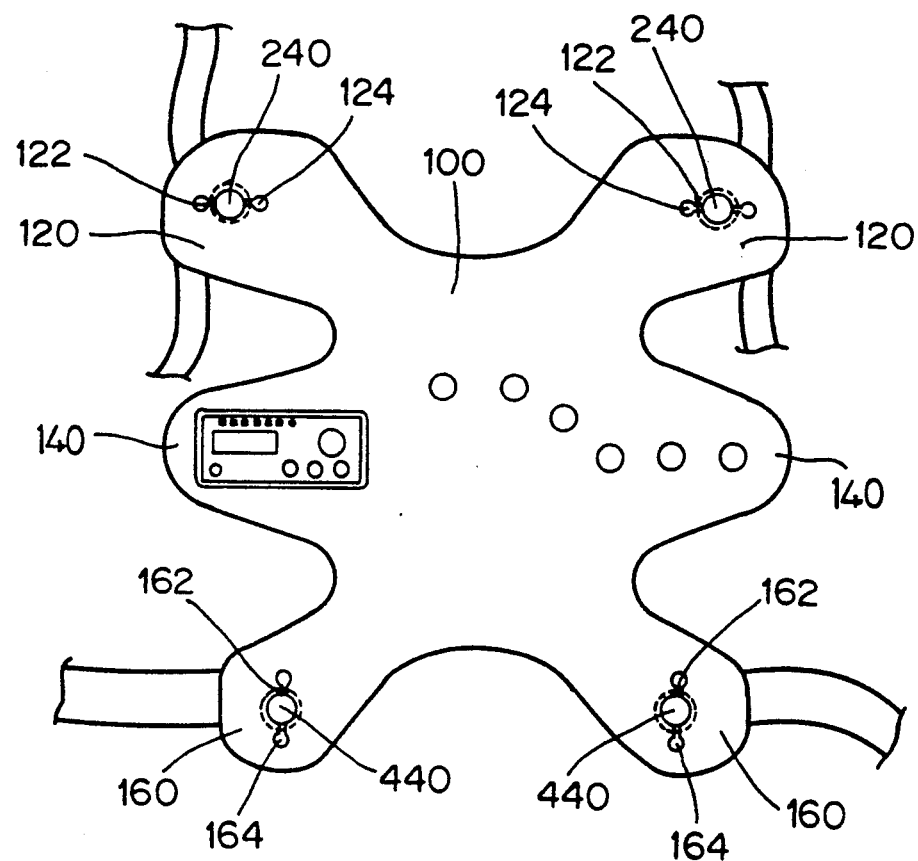
FIG. 5 is a front view of another embodiment of this invention.

The upper and lower limb lead electrodes on the upper and lower fit portions of the pad base may be disposed movably so as to enable the relative locations of these electrodes to be adjusted to the size of the subject's body. That is to say, the pad base 100 is provided in the upper and lower fit portions 120, 160 with guide slits 122, 162 so that the electrodes 240, 440 can be moved along the guide slits 122, 162, as illustrated in FIG. 5. The guide slits 122 in the upper fit portions 120 are arranged horizontally, and the guide slits 162 in the lower fit portions 160 are arranged vertically.

Figure 6:
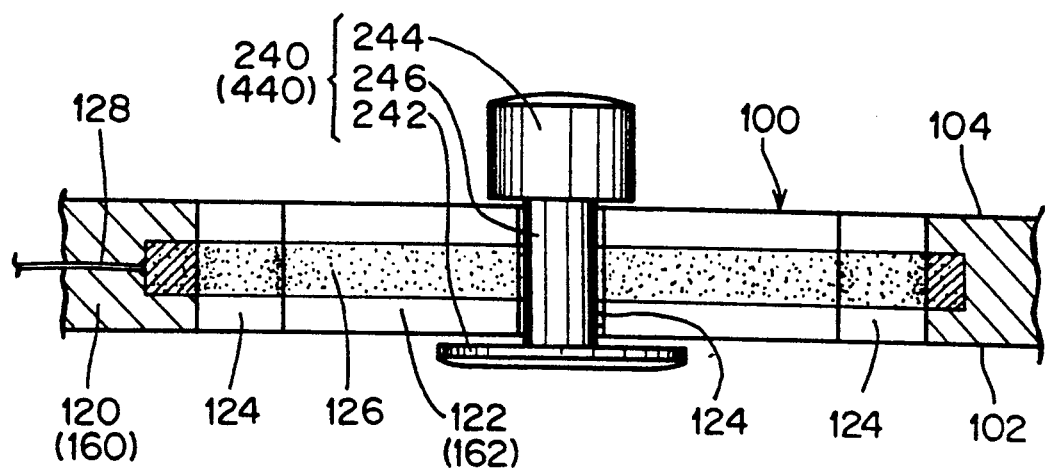
FIG. 6 is a sectioned side view of the limb lead electrode used in the pad of FIG. 5.

The limb lead electrodes 240 (440) on the upper and lower fit portions 120, 160 each comprise a conductor 242 exposed to the inner side of the pad base 100, a nonconductive knob member 244 on the outer side of the pad base, and a conductive connector rod 246 for connecting the conductor 242 and knob member 244, as shown in FIG. 6. The guide slit 122 (162) has a width somewhat smaller than the diameter of the connector rod 246 and is provided with rest holes 124 larger in diameter than the connector rod 246, so that the connector rod 246 is held securely in position inside the guide slit 122 (162).

A conductor layer 126 is exposed to the inside of each guide slit 122 (162) and contacted electrically to the aforenoted ECG control unit by means of a lead cable 128 lying through the interior of pad base 100. The conductor layer 126 may be formed of conductive synthetic rubber or the like. The structure of establishing an electrical connection between each lead electrode 240 (440) and the ECG control unit is not limited only to the illustrated embodiment and may of course be composed of any other means.

In the pad base 100 shown in FIG. 5, the upper, central and lower fit portions 120, 140, 160 are made roundish. As touched upon above, the pad base may be made of porous synthetic resin or a material having air permeability.

As is clear from the foregoing description, the ECG diagnostic pad according to this invention can be readily attached to the chest wall of the subject's body so as to bring the ECG lead electrodes in contact with the desired locations anatomically prescribed on the chest wall with accuracy without the help of a doctor or other helpers. Besides, standard 12-lead ECG data can automatically be detected without fail and reliably recorded over a long time.

As many apparently widely different embodiments of this invention may be made without departing from the spirit and scope thereof, it is to be understood that the invention is not limited to the specific embodiments thereof except as defined in the appended claims.

What is claimed is:

1. An ECG diagnostic pad comprising:

a pad base having a pair of upper fit portions extending aslant upward and each having an upper limb lead electrode for detecting a limb lead ECG current, a pair of central fit portions extending horizontally, and a pair of lower fit portions extending aslant downward and each having a flank lead electrode for detecting a lead ECG current, said upper, central, and lower fit portions being attached to a central portion of said pad base so as to form an asterisk shape; one of said pair of central fit portions being provided with unipolar precordial lead electrodes for detecting precordial lead ECG currents, and the other of said pair of central fit portions being provided with an ECG control unit connected to said lead electrodes for receiving ECG currents from the lead electrodes and for deriving ECG data signals for diagnosis from said ECG currents; and a fastening means attached to said upper, central and lower fit portions for fixing said pad base onto a subject.

2. The ECG diagnostic pad according to claim 1, wherein said fastening means comprises two sets of fastening belts connected to said upper fit portions, each set of fastening belts being wound on an upper arm of a subject to which the pad is attached to, one set of fastening belts connected to said central fit portions, and two sets of fastening belts connected to said lower fit portions, each of said fastening belts having a free end with a surface fastener.

3. The ECG diagnostic pad according to claim 1 wherein said lead electrodes on said upper, central and lower fit portions each comprise a conductive holder, a movable conductor mounted in the holder, and a spring for urging said movable conductor outward.

4. The ECG diagnostic pad according to claim 1 wherein said ECG control unit comprises an ECG input circuit including buffers for receiving the ECG currents from said lead electrodes, an amplifier for amplifying said ECG currents from said ECG input circuit, a time-constant setting circuit for controlling low-frequency characteristics of said ECG currents, a multiplexer for feeding out said ECG currents from said amplifier one by one in serial order, an analog-digital converter for converting said ECG current to digital signals, a demodulator for distributing said digital signals into twelve ECG data signals, digital-analog converters for converting said ECG data signals to analog ECG signals, an output-stage multiplexer for synthesizing said analog ECG signals, and a sound driver for driving a sound generator.

5. The ECG diagnostic pad according to claim 4, further comprising a recording means electrically connected to said ECG control unit for recording said ECG data signals.

6. The ECG diagnostic pad according to claim 5, wherein said recording means is mounted on said fastening means.

7. The ECG diagnostic pad according to claim 6, wherein said recording means is provided with a power battery unit.

8. The ECG diagnostic pad according to claim 1, further comprising a recording means electrically connected to said ECG control unit for recording said ECG data signals.

9. The ECG diagnostic pad according to claim 8, wherein said recording means is mounted on said fastening means.

10. The ECG diagnostic pad according to claim 9, wherein said recording means is provided with a power battery unit.

11. The ECG diagnostic pad according to claim 1 wherein said pad base is provided in said upper and lower fit portions with guide slits in which said upper limb lead electrodes and flank lead electrodes are fitted movably.

12. The ECG diagnostic pad according to claim 11 wherein said lead electrodes on said upper and lower fit portions each comprise a conductor, a nonconductive knob member, and a conductive connector rod connecting said conductor to said knob member.

13. The ECG diagnostic pad according to claim 12 wherein each said guide slit has a width somewhat smaller than said connector rod in diameter and has rest holes larger in diameter than said connector rod.

* * * * *